(12) United States Patent
Jensen (10) Patent No.: US 10,448,926 B2
(45) Date of Patent: Oct. 22, 2019

(54) TRANSVERSE OSCILLATION VECTOR ESTIMATION IN ULTRASOUND IMAGING (71) Applicant: B-K Medical Aps, Herlev (DK)

(72) Inventor: Jorgen Jensen, Horsholm (DK)

(73) Assignee: B-K Medical Aps, Herlev (DK)

( * ) Notice: Subject to any disclaimer, the term of this patent is extended or adjusted under 35 U.S.C. 154(b) by 805 days.

(21) Appl. No.: 15/054,339

(22) Filed: Feb. 26, 2016

(65) Prior Publication Data

US 2017/0245833 A1 Aug. 31, 2017

(51) Int. Cl.
*A61B 8/08* (2006.01)
*A61B 8/00* (2006.01)
*A61B 8/06* (2006.01)
*G01S 15/89* (2006.01)
*G01S 7/52* (2006.01)

(52) U.S. Cl.
CPC .............. *A61B 8/5223* (2013.01); *A61B 8/06* (2013.01); *A61B 8/463* (2013.01); *A61B 8/5207* (2013.01); *G01S 7/52042* (2013.01); *G01S 15/8927* (2013.01); *G01S 15/8984* (2013.01); *G01S 15/8993* (2013.01)

(58) Field of Classification Search
CPC ........... A61B 8/5223; A61B 8/00; A61B 8/06; A61B 8/5207; A61B 8/463; G01S 15/8984; G01S 7/00; G01S 15/00; G01S 7/52042; G01S 15/8927; G01S 15/8993
See application file for complete search history.

(56) References Cited

U.S. PATENT DOCUMENTS

| 5,119,821 | A | * | 6/1992 | Tuchler | A61B 8/06 600/454 |
| 5,409,010 | A | * | 4/1995 | Beach | A61B 8/06 600/455 |
| 6,135,957 | A | * | 10/2000 | Cohen-Bacrie | G01P 5/244 600/370 |
| 6,148,224 | A | * | 11/2000 | Jensen | G01P 3/64 324/306 |

(Continued)

OTHER PUBLICATIONS

Jensen, Jørgen Arendt. "A new estimator for vector velocity estimation [medical ultrasonics]." IEEE transactions on ultrasonics, ferroelectrics, and frequency control 48.4 (2001): 886-894. (Year: 2001).*

(Continued)

*Primary Examiner* — Amelie R Gillman
*Assistant Examiner* — Sean D Mattson
(74) *Attorney, Agent, or Firm* — Anthony M. Del Zoppo, III; Daugherty & Del Zoppo Co. LPA (57) ABSTRACT

Continuously transmitting, with a transducer array, an ultrasound signal in one direction beamforming, with a beamformer, an echo signal received by the transducer array using on a predetermined apodization function, wherein the echo signal is generated in response to an interaction of the ultrasound signal with flowing structure estimating, with a velocity processor, a vector velocity of the flow, including velocity components, as a function of depth and time from the beamformed echo signals using transverse oscillation vector velocity estimation, generating, with a measurement processor, a quantitative measurement from the velocity components, and visually displaying, with a display monitor, the quantitative measurement.

27 Claims, 5 Drawing Sheets

(56) References Cited

U.S. PATENT DOCUMENTS

| | | | | |
|---|---|---|---|---|
| 6,535,835 | B1* | 3/2003 | Rubin | A61B 8/06 702/159 |
| 6,859,659 | B1 | 2/2005 | Jensen | |
| 2002/0151795 | A1* | 10/2002 | Palti | A61B 8/06 600/454 |
| 2011/0196237 | A1* | 8/2011 | Pelissier | A61B 8/06 600/454 |
| 2014/0056099 | A1* | 2/2014 | Hancock | A61B 8/5207 367/11 |
| 2014/0257103 | A1* | 9/2014 | Jensen | G01P 5/244 600/441 |

OTHER PUBLICATIONS

Udesen, Jesper, and Jørgen Arendt Jensen. "Investigation of transverse oscillation method." IEEE transactions on ultrasonics, ferroelectrics, and frequency control 53.5 (2006): 959-971. (Year: 2006).*

Anderson, Martin E., Multi-Dimensional Velocity Estimation with Ultrasound Using Spatial Quadrature, IEEE, vol. 45, No. 3, May 1998.

Anderson, T. and McDicken, W. N., Measurement of tissue motion, Proc. Instn. Mech. Engrs. vol. 213, Part H, 1999.

Basarab, Adrian, et al., Phase-Based Block Matching Applied to Motion Estimation with Unconventional Beamforming Strategies, IEEE, vol. 56, No. 5, May 2009.

Jensen, Jorgen Arendt, A New Estimator for Vector Velocity Estimation, IEEE, vol. 48, No. 4, Jul. 2001.

Jensen, Jorgen Arendt, Optimization of Transverse Oscillating Fields for Vector Velocity Estimation with Convex Arrays, 2013 Joint UFFC, EFTF and PFM Symposium.

Jensen, Jorgen Arendt, Transverse Spectral Velocity Estimation, IEEE vol. 61, No. 11, Nov. 2014.

Jensen, Jonas et al., Accuracy and Sources of Error for an Angle Independent Volume Flow Estimator, Ultrasonics Symposium (IUS) 2014 IEEE International, pp. 1714-1717, Sep. 3-6, 2014.

Jensen, Jorgen and Munk, Peter, A New Method for Estimation of Velocity Vectors, IEEE vol. 45, No. 3, May 1998.

Kasai, C., et al., Real-Time Two-Dimensional Blood Flow Imaging Using an Autocorrelation Technique, IEEE vol. SU-32, No. 3, May 1985.

Liebgott, H. et al., PSF Dedicated to Estimation of Displacement Vectors for Tissue Elasticity Imaging with Ultrasound, IEEE vol. 54, No. 4, Apr. 2007.

Liebgott, H., et al., Correspondence—Lateral RF Image Synthesis Using a Synthetic Aperture Imaging Technique, IEEE vol. 55, No. 9, Sep. 2008.

Newhouse, V., et al., The Dependence of ultrasound Doppler Bandwidth on Beam Geometry, IEEE vol. SU-27, No. 2, Mar. 1980.

Olesen, J., et al., Noninvasive Estimation of 2-D Pressure Gradients in Steady Flow Using Ultrasound, IEEE vol. 61, No. 8, Aug. 2014.

Olesen, J., et al., Non-invasive Estimation of Pressure Gradients in Pulsatile Flow using Ultrasound, 2014 IEEE International Ultrasonics Symposium Proceedings.

Ophir, J., et al., Elastography: Imaging the Elastic Properties of Soft Tissues with Ultrasound, J Med Ultrasonics 2002;29 (Winter): 155-171.

Pihl, M. J., A Transverse Oscillation Approach for Estimation of Three-Dimensional Velocity Vectors, Part II: Experimental Validation, IEEE vol. 61, No. 10, Oct. 2014.

Pihl, M. J., A Transverse Oscillation Approach for Estimation of Three-Dimensional Velocity Vectors, Part I: Concept and Simulation Study, IEEE vol. 61, No. 10, Oct. 2014.

Sumi, C., Displacement Vector Measurement Using Instantaneous Ultrasound Signal Phase—Multidimensional Autocorrelation and Doppler Methods, IEEE vol. 55, No. 1, Jan. 2008.

* cited by examiner

TRANSVERSE OSCILLATION VECTOR ESTIMATION IN ULTRASOUND IMAGING

TECHNICAL FIELD

The following generally relates to ultrasound imaging and more particularly to a transverse oscillation vector velocity estimation in ultrasound imaging.

BACKGROUND

Ultrasound imaging provides useful information about the interior characteristics of an object or a subject. In one instance, ultrasound imaging is used to generate both an image of the interior characteristics and estimate flow velocity of flowing structure (e.g., blood cells and tissue motion), and display the image with indicia indicative of the estimated flow velocity superimposed there over. An example ultrasound system uses power Doppler or color flow mapping to identify places of flow, and subsequently uses spectral velocity estimation for determining quantitative measures. For this, ultrasound pulses are emitted continuously in one direction and segments of data are Fourier transformed to yield the velocity distribution from which quantitative velocity measures can be found. An example of this is described in Jensen, "Estimation of Blood Velocities Using Ultrasound: A Signal Processing Approach," Cambridge University Press, New York, 1996.

However, this approach has several drawbacks. For example, with this approach the velocity is only computed in the axial (or beam) direction and must be angle corrected to yield the velocity magnitude. Most often vessels are parallel to the skin surface and the beam-to-flow angle is close to ninety (90) degrees, making the angle correction unreliable and error prone. The spectral estimates also suffer from spectral broadening artifacts from the segmentation and windowing of the data. A consistent over-estimation of peak and mean velocities are therefore often found. Furthermore, the maximum velocity detectable is limited by the pulse repetition frequency and the employed wavelength, which are fixed. This in combination with the length of the segments used gives the lowest velocity detectable and hence the velocity range, which can be estimated during a single measurement.

SUMMARY

Aspects of the application address the above matters, and others.

In one aspect, a method includes continuously transmitting, with a transducer array, an ultrasound signal in one direction. The method further includes beamforming, with a beamformer, an echo signal received by the transducer array using on a predetermined apodization function. The echo signal is generated in response to an interaction of the ultrasound signal with flowing structure. The method further includes estimating, with a velocity processor, a vector velocity of the flow, including velocity components, as a function of depth and time from the beamformed echo signals using transverse oscillation vector velocity estimation. The method further includes generating, with a measurement processor, a quantitative measurement from the velocity components. The method further includes visually displaying, with a display monitor, the quantitative measurement.

In another aspect, an ultrasound imaging system includes a transducer array configured to continuously transmit an ultrasound signal in one direction. The ultrasound imaging system further includes a beamformer configured to beamform echo signals received by the transducer array using on a predetermined apodization function. The ultrasound imaging system further includes a velocity processor configured to determine a vector velocity of flow, including velocity components, from the beamformed echo signals using transverse oscillation vector velocity estimation. The ultrasound imaging system further includes a measurement processor configured to generate a quantitative measurement from the velocity components. The ultrasound imaging system further includes a display that visually presents the quantitative measurement.

In another aspect, an apparatus includes a beamformer configured to beamform, using on a predetermined apodization function, echo signals received by a transducer array of an ultrasound imaging system. The echo signals are generated in response to an interaction of anatomical tissue and an ultrasound signal continuously transmitted by the transducer array in one direction. The apodization function includes a selectable parameter that controls a maximum measurable velocity. The apparatus further includes a controller that sets the selectable parameter based on whether a first or a second vector velocity is being measured, wherein the first vector velocity is greater than the second vector velocity. The apparatus further includes a processor configured to determine the vector velocity, including velocity components, from the beamformed echo signals using transverse oscillation vector velocity estimation. The apparatus further includes a display that visually presents the quantitative measurement.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
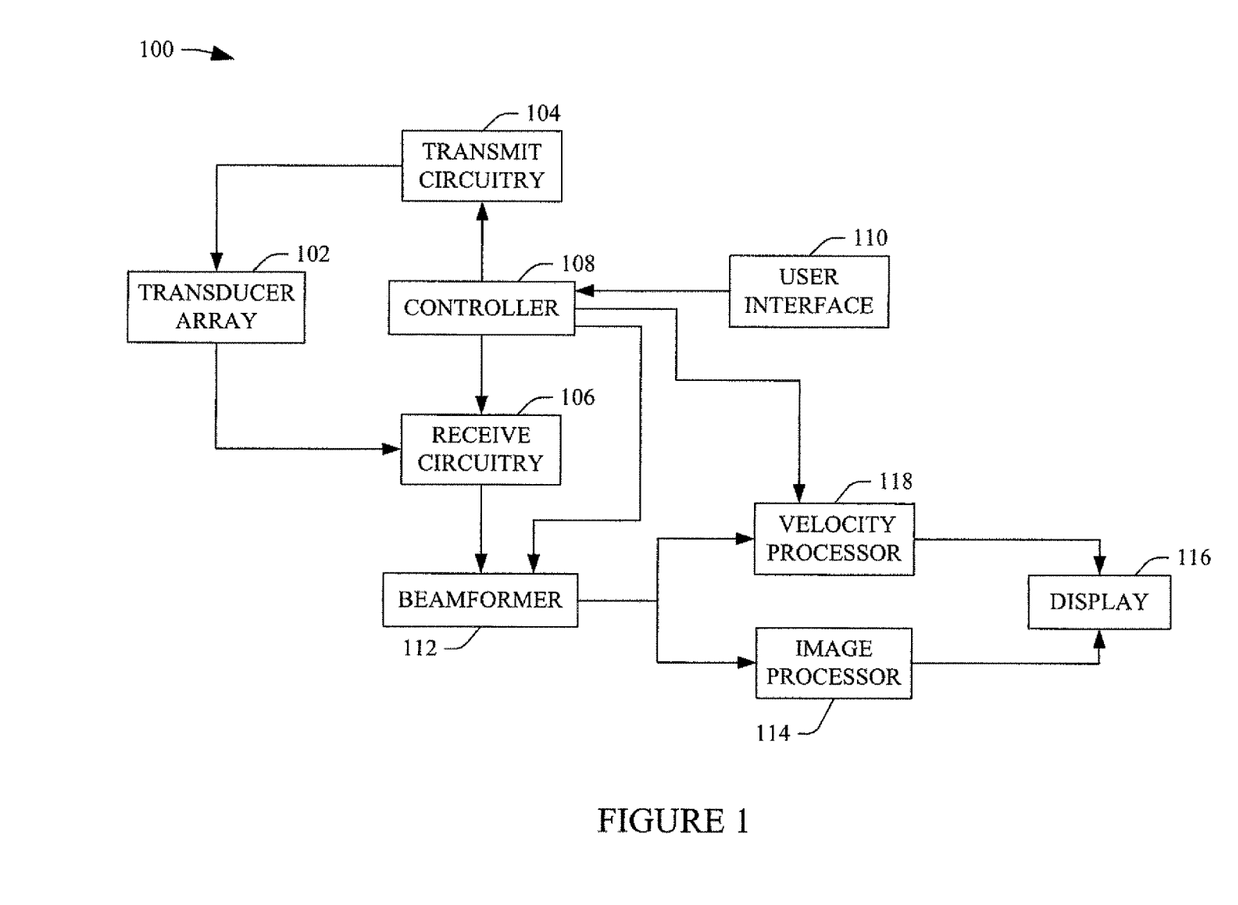
FIG. 1 schematically illustrates an example ultrasound imaging system configured for transverse oscillation vector flow imaging (TO VFI)

Initially referring to FIG. 1, an example ultrasound imaging system 100 is illustrated.

A transducer array 102 includes a one-dimensional (1-D) array or a two dimensional (2-D) array of transducer elements, which are configured to transmit ultrasound signals, receive echo signals and generate electrical signals indicative of the received echo signals. Examples of 1-D arrays include 16, 32, 64, 128, 256, etc., and examples of 2-D arrays include 32×32, 64×64, etc., 2-D row column matrix arrays and/or other dimension arrays, including circular, elliptical, rectangular, irregular, etc. The transducer array 102 can be linear, curved, and/or otherwise shaped, fully populated, sparse, row-column, etc.

Transmit circuitry 104 generates a set of pulses that are conveyed to the transducer array 102. The set of pulses invokes a set of the transducer elements to transmit ultrasound signals. In a continuous emission mode, the set of pulses invokes the transducer array 102 to continuously emit ultrasound signals in one direction. Receive circuitry 106 receives electrical signals from the transducer array 102, which are indicative of received echoes, which, generally, are a result of the interaction between the transmitted ultrasound signals and the structure such as flowing blood cells, organ cells, soft tissue, etc.

A controller 108 controls one or more of the transmit circuitry 104 and/or the receive circuitry 106. Such control can be based on available modes of operation such as the continuous emission with vector velocity estimation as a function of depth using a 2-D or a 3-D transverse oscillation (TO) mode, a B-mode, a measurement mode (e.g., volume flow, pressure gradient, velocity profile, laminar flow, etc.), and/or other mode. Such control can be selected based on one or more signals indicative of input from a user via a user interface (UI) 110. The UI 110 may include one or more input devices (e.g., a button, a knob, a slider, a touch pad, etc.) and/or one or more output devices (e.g., a display screen, lights, a speaker, etc.).

Figure 2:
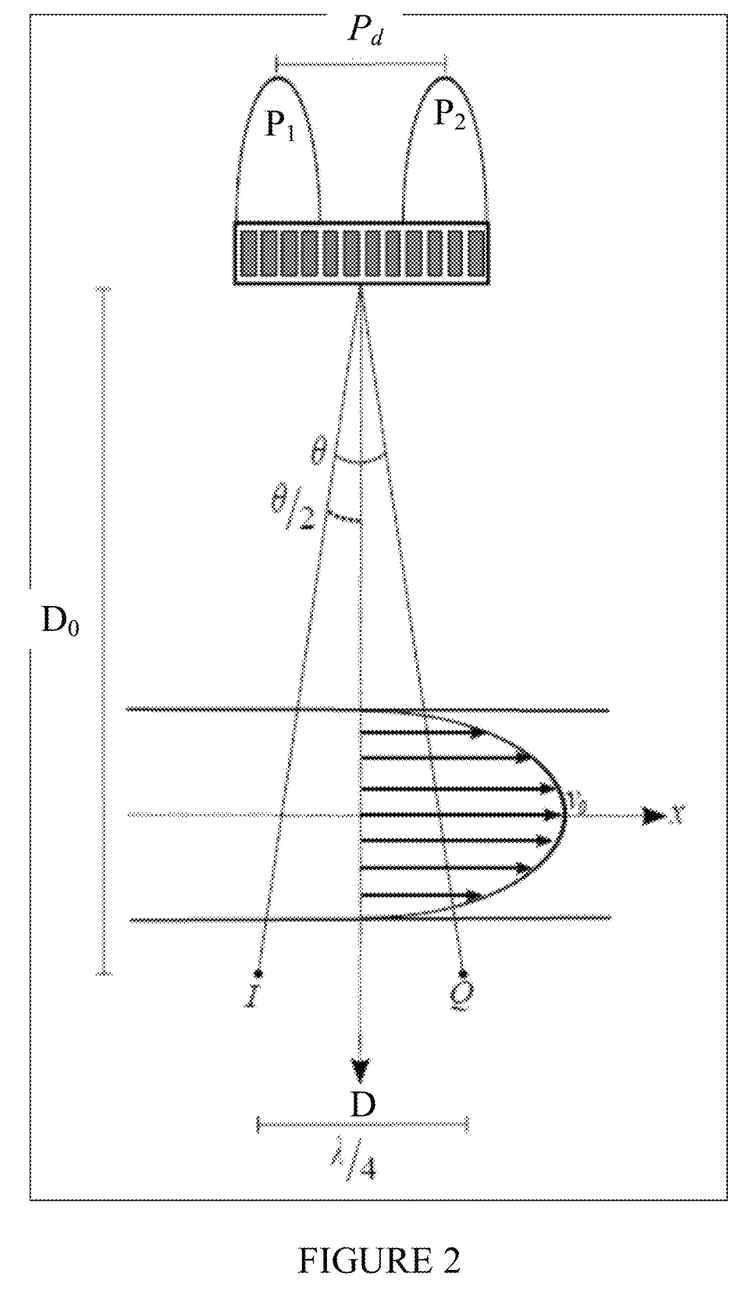
FIG. 2 schematically illustrates a transverse oscillation approach for determining a vector velocity, including axial and lateral velocity components, with a 1-D transducer array.

A beamformer 112 processes the electrical signals and produces data used to generate at least an image and a vector velocity estimate. For a B-mode image, the beamformer 112 processes the signals by applying time delays, weighting the channels, and summing the weighted delayed signal, and/or otherwise beamforming the signals. For TO vector velocity imaging (VFI), the beamformer 112 beamforms beams to produce spatial lateral in-phase (I) and quadrature (Q) components. An example for 1-D TO is shown in FIG. 2. A transverse oscillation is introduced in the ultrasound field, and this oscillation generates received signals that depend on the transverse oscillation. The basic idea is to create a double-oscillating pulse-echo field and use a particular apodization profile(s) in receive beamforming. The spatial IQ samples, $r_1$, $r_2$ are obtained by $r_1(n) = r_I(n) + jr_Q(n)$ and $r_2(n) = r_I(n) - jr_Q(n)$, where $r_I$ and $r_Q$ are the samples at index n from the left and right beams, respectively. The two beams are phased shifted a quarter of the lateral wavelength. A center beam is beamformed for axial velocity estimation.

Returning to FIG. 1, an image processor 114 processes the beamformed data and generates a sequence of focused, coherent echo samples along focused scanlines of a scanplane, or a B-mode image. The image processor 114 may also be configured to process the scanlines to lower speckle and/or improve specular reflector delineation via spatial compounding and/or perform other processing such as FIR filtering, IIR filtering, etc. The B-mode image can be displayed via a display 116. This can be, e.g., in a graphical user interface (GUI), which allows a user to selectively rotate, scale, manipulate, take measurements on, etc. the displayed data. This can be through a mouse, a keyboard, a touchscreen and/or the like.

Figure 3:
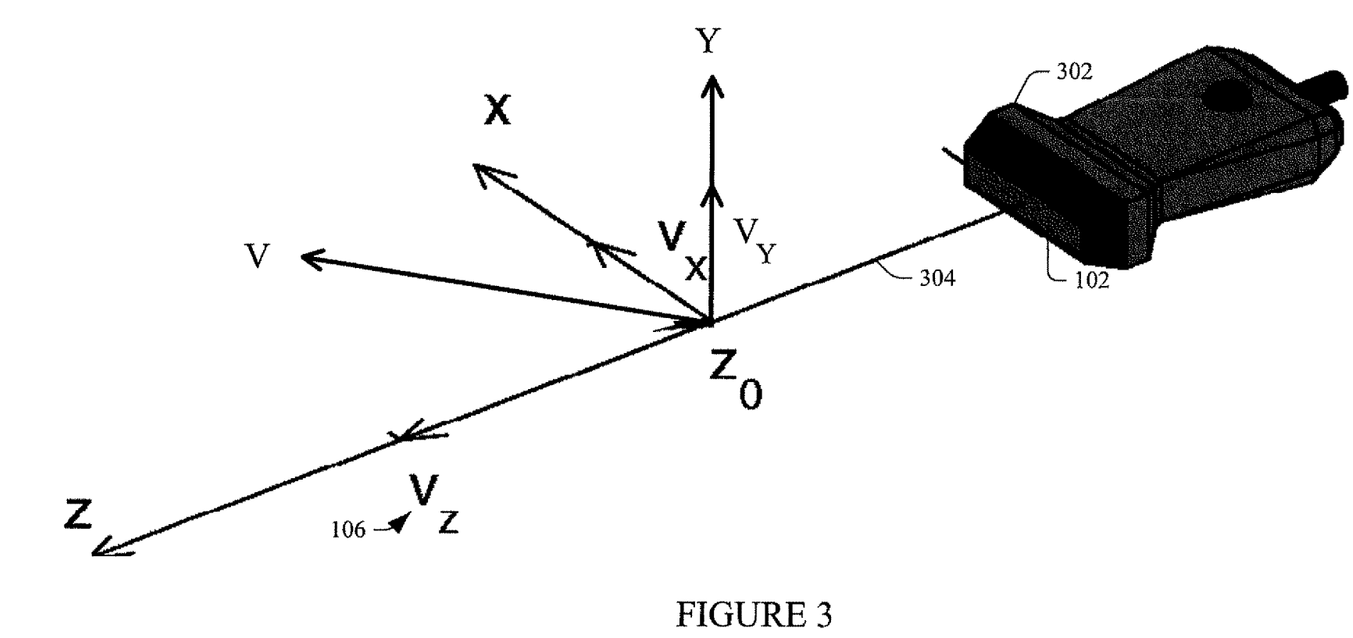
FIG. 3 schematically illustrates an ultrasound beam and vector velocity components from a scatterer.

A velocity processor 118 processes the beamformed data to estimate a vector velocity. The velocity processor 118 is configured to determine a vector velocity (v), an axial velocity component (vz) and a lateral velocity component (vx) for TO VFI with a 1-D array, and the vector velocity (v), the axial velocity component (vz), the lateral velocity component (vx) and an elevation velocity component (vy) for TO VFI with a 2-D array. Vector velocity components for three dimensions are shown in FIG. 3 in relation to the transducer array 102, which is housed in and/or part of a probe 302. FIG. 3 shows v, vz along a direction of a beam 304, vx which is perpendicular to vz, and vy which is perpendicular to vz and vx.

Examples of suitable velocity processing are described in U.S. Pat. No. 6,148,224 A, titled "Apparatus and method for determining movements and velocities of moving objects," and filed Dec. 30, 1998, U.S. Pat. No. 6,859,659 A, titled "Estimation of vector velocity," and filed May 10, 2000, and patent application US 2014/0257103 A1, titled "Three Dimensional (3D) Transverse Oscillation Vector Velocity Ultrasound Imaging," and filed Oct. 11, 2011, the entireties of which are all incorporated herein by reference. In general, the velocity components vx or vy can be determined as shown below in Equations 4 and 5:

$$vx = \left(\frac{\lambda_x}{2\pi 2kT_{prf}}\right) \arctan\left(\frac{\mathcal{J}\{R_1(k)\}\mathcal{R}\{R_2(k)\} + \mathcal{J}\{R_2(k)\}\mathcal{R}\{R_1(k)\}}{\mathcal{R}\{R_1(k)\}\mathcal{R}\{R_2(k)\} - \mathcal{J}\{R_2(k)\}\mathcal{J}\{R_1(k)\}}\right), \text{ and} \quad \text{Equation 4}$$

$$vy = \left(\frac{\lambda_y}{2\pi 2kT_{prf}}\right) \arctan\left(\frac{\mathcal{J}\{R_1(k)\}\mathcal{R}\{R_2(k)\} + \mathcal{J}\{R_2(k)\}\mathcal{R}\{R_1(k)\}}{\mathcal{R}\{R_1(k)\}\mathcal{R}\{R_2(k)\} - \mathcal{J}\{R_2(k)\}\mathcal{J}\{R_1(k)\}}\right), \quad \text{Equation 5}$$

where $T_{prf}$ is the time between two pulses, $R_1(k)$ is the complex lag k autocorrelation value for $r_1(n)$, and $R_2(k)$ is the complex lag k autocorrelation value for $r_2(n)$.

From the continuous stream of data, the velocity processor 118 continuously estimates a vector velocity via TO VFI. The velocity processor 118 can expand the velocity range and accuracy as described next. For sake of brevity and clarity, the following is described in connection with a 1-D transducer array. However, one of ordinary skill in the art would be able to apply this to application using a 2-D transducer array in view of the description herein and without undue experimentation. Briefly turning back to FIG. 2, the lateral wavelength $\lambda_x$ can be predicted from Equation 1:

$$\lambda_x = \frac{2\lambda D}{P_d} = \frac{2\lambda D}{N_d P_i}, \quad \text{Equation 1}$$

where $\lambda$ is an axial wavelength, D is a depth, $P_d$ is a distance between peaks $P_1$ and $P_2$ in the apodization function, $P_i$ is a transducer pitch, and $N_d$ a number of elements between the peaks $P_1$ and $P_2$. The lateral wavelength $\lambda_x$ depends on $P_d$ in the receive apodization function.

In a conventional ultrasound system using an autocorrelation approach, such as the one described in Kasai et al., "Real-Time Two-Dimensional Blood Flow Imaging using an Autocorrelation Technique," IEEE Trans. Son. Ultrason., 32:458-463, 1985, the maximum detectable velocity $v_{max}$ can be determined as shown in Equation 2:

$$v_{max} = \frac{\lambda f_{prf}}{4} \quad \text{Equation 2}$$

where $$f_{prf} \left(\text{i.e., } \frac{1}{T_{prf}}\right)$$

is a pulse repetition frequency. For the TO approach described herein, the maximum velocity estimate is determined by the lateral wavelength $\lambda_x$ and the pulse repetition frequency as shown in Equation 3:

$$v_{max} = \frac{\lambda_x f_{prf}}{4}. \qquad \text{Equation 3}$$

The lateral wavelength $\lambda_x$ can be changed by changing $P_d$ in Equation 1. For higher velocities, a smaller value of $P_d$ is selected to yield a $\lambda_x$ four (4) to eight (8) times $\lambda$ and, thus, yielding a maximum velocity four to eight times larger than in a conventional system. The velocity can also be estimated with a low bias as described in Jensen, "Optimization of transverse oscillating fields for vector velocity estimation with convex arrays," In Proc. IEEE Ultrason. Symp., pages 1753-1756, July 2013. For lower velocities, a larger value of $P_d$ is selected to make the estimation better as the lateral oscillation period is adapted to low velocity estimation by having a lower $\lambda_x$. The variation in $P_d$ is achieved during receive beam forming and set by the controller 108.

The velocity processor 118 can employ one or more different receive apodization functions to estimate low and high velocities simultaneously from the same data. The velocity processor 118 can also adapt the apodization over time to both yield both high systolic velocities as well as low diastolic velocities for the same data. The velocity processor 118 can also retrospectively change the velocity range automatically and/or with user intervention. This can be combined with directional TO to make itself calibrating and to increase accuracy. An example of directional TO is described in patent application PCT/IB2015/051526, titled "Ultrasound Imaging Flow Vector Velocity Estimation with Directional Transverse Oscillation," and filed Mar. 2, 2015, the entirety of which is incorporated herein by reference.

The approach described herein avoids spectral broadening seen in spectral estimates from windowing, allowing for yielding truly quantitative data with automatic angle estimation, as both the axial and transverse velocities are estimated. The same data can also be processed to simultaneously compute and display the TO velocity, a spectrogram, and a transverse spectrogram as discussed in patent application US 20150331103 A1, titled "Angle independent velocity spectrum determination," and filed Nov. 28, 2012, the entirety of which is incorporated herein by reference, and in Jensen, "Transverse spectral velocity estimation," IEEE Trans. Ultrason., Ferroelec., Freq. Contr., 61(11):1815-1823, November 2014.

Figure 4:
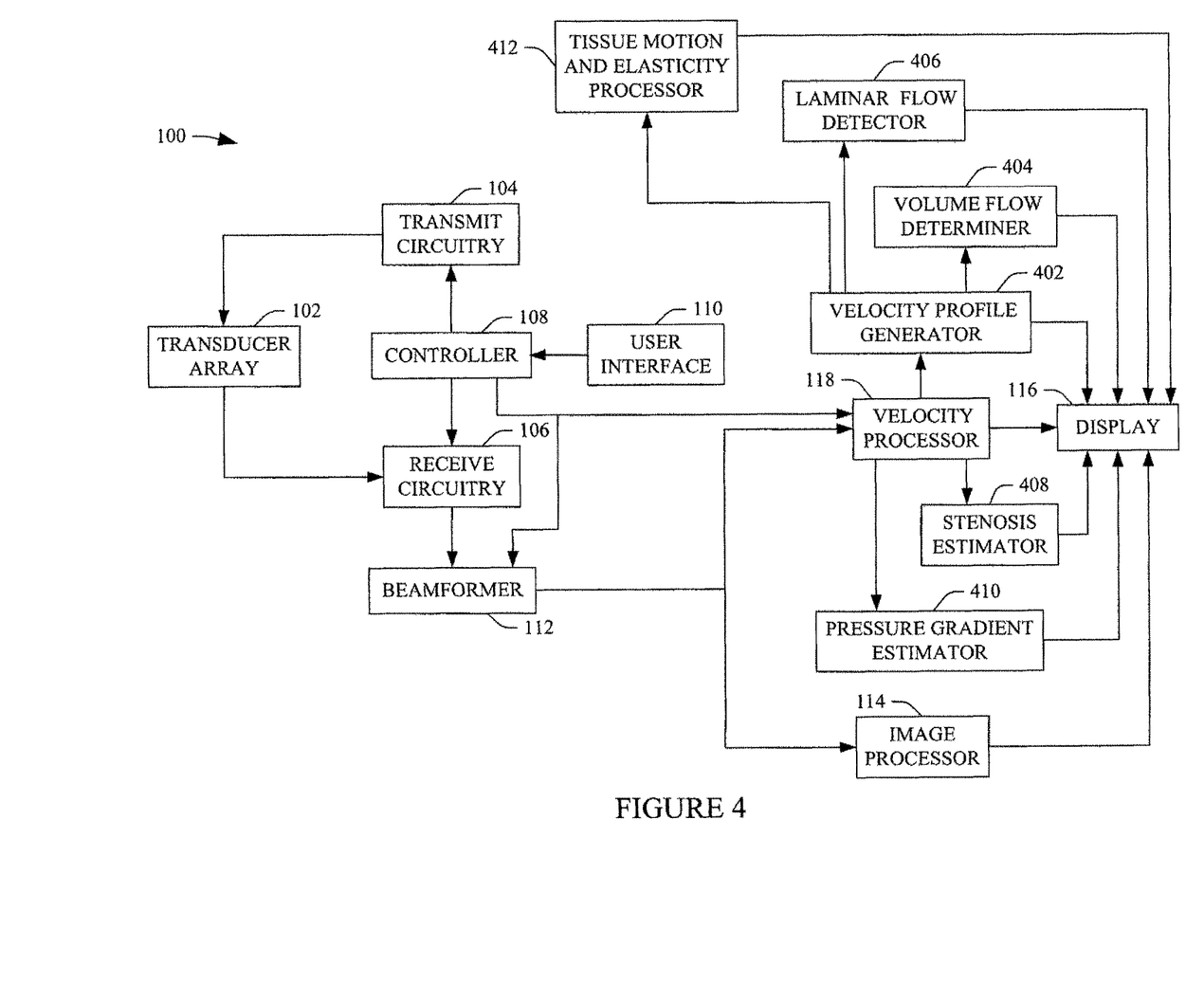
FIG. 4 schematically illustrates a variation of the system of FIG. 1 further configured to make one or more quantitative measurements from the vector velocity.

FIG. 4 shows a variation in which the system 100 of FIG. 1 further includes a velocity profile generator 402. The velocity processor 314 estimates velocities as a function of depth and time as data are measured continuously along the measurement direction. The velocity profile generator 402 processes this data and generate a velocity profile. The velocity profile is then displayed as arrows superimposed on the B-mode image, in other time-depth-velocity displays, etc. The velocity profile generator 402 can compute and display a velocity magnitude and/or an angle as a function of time or depth form the velocity profile.

FIG. 4 further includes a volume flow determiner 404 which directly calculate the volume flow for a vessel from the velocity profile. For this, boundaries of a vessel are marked or estimated on the B-mode image, and a center position of the vessel is determined, automatically and/or manually be a user. Assuming a circular vessel, the volume flow Q is found by integrating the velocities weighted by the area at the give depth as show in Equation 6:

$$Q = \pi \Delta r \sum_{n=-N/2}^{N/2} |n| \vec{v}(n) \cdot \vec{e}, \qquad \text{Equation 6}$$

where $\Delta r$ is the radial sampling interval, N is the number of intervals within the vessel, $\vec{v}(n)$ is the velocity at sample n, and $\vec{e}$ is the unit vector for the plane to find the volume flow through. An elliptical vessel dimensions can be determined from the B-mode image perpendicular to the velocity view to find a major axis $d_2$ and a minor axis $d_1$. The volume flow is then computed by as shown in Equation 7:

$$Q = \frac{d_2}{d_1} \pi \Delta r \sum_{n=-N/2}^{N/2} |n| \vec{v}(n) \cdot \vec{e}. \qquad \text{Equation 7}$$

FIG. 4 further includes a laminar flow detector 406 that can detect presence and/or absence of laminar flow from the velocity angle determined by the velocity profile generator 402. Generally, a stable angle over time shows that laminar flow is present, and deviations from the mean angle is an indication of disturbed or turbulent flow. The angle for a fully turbulent flow will randomly fluctuate between $-\pi$ to $+\pi$ with a rectangular probability density, which has a variance of $$\sigma_\theta^2 = \frac{(2\pi)^2}{12} = \frac{\pi^2}{3}.$$

An index $L_i$ for indicating whether the flow is laminar is as shown in Equation 8:

$$L_i = 1 - \sqrt{\frac{\hat{\sigma}_\theta^2}{\frac{\pi^2}{3}}} = 1 - \sqrt{\frac{\frac{1}{N}\sum_{n=1}^{N_\theta}\left(\hat{\theta}(n) - E\{\hat{\theta}(n)\}\right)^2}{\frac{\pi^2}{3}}} \qquad \text{Equation 8}$$

where $\theta$ is the beam to flow angle, $\hat{\theta}(n)$ is the velocity angles estimate, $\hat{\sigma}_\theta^2$ is the estimated angle variance, and $E\{\ \}$ denotes mean value, and $N_\theta$ is the number of estimates averaged over in either time or space or both. A value of one (1) indicates a fully laminar flow with no angle variation, whereas a value of zero (0) is for fully turbulent flow. The index can be found over time and averaged, averaged over space, etc. It can also be used for displaying a turbulence map.

FIG. 4 further includes a stenosis estimator 408. The stenosis estimator 408 can determine a degree of stenosis in a vessel from a ratio between vector velocities measured before and at the stenosis. The approach described herein has a higher maximum velocity than for spectral estimation and can measure at two different places intermixed, and still have a sufficient velocity range for making a reliable index. The beams are placed at the stenosis and before it, and the velocity ratio is determined.

In one instance, the stenosis estimator 408 determines the stenosis degree as shown in Equation 9:

$$s_d = 1 - \sqrt{\frac{r_1}{r_2}} \qquad \text{Equation 9}$$

where $r_1$ is a radius at the stenosis and $r_2$ is a radius at the non-stenosed part of the vessel. Assuming a parabolic velocity profile the stenosis degree can be determined as shown in Equation 10:

$$s_d = 1 - \sqrt{\frac{v_1}{v_2}} \qquad \text{Equation 10}$$

where $v_1$ is a velocity measured at the stenosis and $v_2$ is a velocity measured at the non-stenosed part of the vessel. The velocities can be the mean, peak, instantaneous and/or other velocity and/or averaged values of these over time and/or space. The stenosis degree is estimated as shown in Equation 11:

$$s_d = 1 - \sqrt{\frac{v_2}{2v_1}} \qquad \text{Equation 11}$$

if a plug flow is assumed in the vessel. The flow type (parabolic/plug or in between) can be determined from the velocity profile measured by the approach described.

FIG. 4 further includes a pressure gradient estimator 410. The pressure gradient estimator 410 can determine pressure gradients in vessels by solving the Navier-Stokes equation and determining and using temporal and spatial acceleration of the flow. These can be derived from sending out a broad beam in transmit and then focus around two directions in receive. This will give data suitable for both deriving the temporal and spatial accelerations due to the continuous acquisition. The spatial acceleration is derived based on velocity estimates from both the two adjacent beams and the estimates as a function of depth to yield spatial accelerations in two directions.

Examples are described in Jensen et e., "Accuracy and sources of error for an angle independent volume flow estimator," Proc. IEEE Ultrason. Symp., pages 1714-1717, Olesen et al., "Noninvasive estimation of 2-D pressure gradients in steady flow using ultrasound," IEEE Trans. Ultrason., Ferroelec., Freq. Contr., patent application PCT/IB2015/054246, titled "Non-invasive Estimation of Intravascular Pressure Changes using Vector Velocity Ultrasound (US)," and filed Jun. 4, 2015, the entirety of which is incorporated herein by reference, and patent application PCT/IB2015/055592, titled "Flow Acceleration Estimation Directly From Beamformed Ultrasound Data," and filed Jul. 23, 2015, the entirety of which is incorporated herein by reference.

FIG. 4 further includes a tissue motion and elasticity processor 412. The tissue motion and elasticity processor 412 can be employed to both estimate velocities in blood vessel or in the surround tissue to quantify tissue motion from the velocity profile. An example of estimating these parameters from a velocity measurement is as described by Anderson, T., & McDicken, W. N. (1999). Measurement of tissue motion. Proceedings of the Institution of Mechanical Engineers, Journal of Engineering in Medicine, Archive, Proceedings of Institution of Mechanical Engineers, Part H, 213(H3), 181-191. Additionally or alternatively, the tissue motion and elasticity processor 412 can also be used to quantify the elasticity of tissue from the velocity profile. An example of quantifying this parameter from a velocity measurement is described in Ophir et al. "Elastography: Imaging the Elastic Properties of Soft Tissues with Ultrasound.", J. Med. Ultrason 29.4 (2002): 155-171.

It is to be appreciated that one or more of the velocity profile generator 402, the stenosis estimator 408 or the pressure gradient estimator 410 can be omitted. Where the velocity profile generator 402 is omitted, the volume flow determiner 404, the laminar flow detector 406 and the tissue motion and elasticity processor 412 are omitted. Where the velocity profile generator 402 is present, the volume flow determiner 404, the laminar flow detector 406 and/or the tissue motion and elasticity processor 412 are present (or omitted). A combination of one or more of the components 402, 404, 406, 408, 410 and 412 is referred to herein as a measurement processor.

It is also to be appreciated that one or more of the velocity processor 118, the velocity profile generator 402, the volume flow determiner 404, the laminar flow detector 406, the stenosis estimator 408, or the pressure gradient estimator 410 can be implemented by a processor (e.g., a central processing unit, a microprocessor, etc.) executing a computer readable instruction embedded or stored on non-transitory computer readable medium (which excludes transitory computer readable medium) such as physical memory and/or carried by transitory computer readable medium such as a carrier wave, signal, etc.

The ultrasound imaging system 100 can be part of a portable system on a stand with wheels, a system residing on a tabletop, and/or other system in which the transducer array 102 is housed in a probe or the like, and a console is housed in an apparatus separate therefrom. In another instance, the transducer array 102 and the console can be housed in a same apparatus such as within a single enclosure hand-held ultrasound scanning device.

Figure 5:
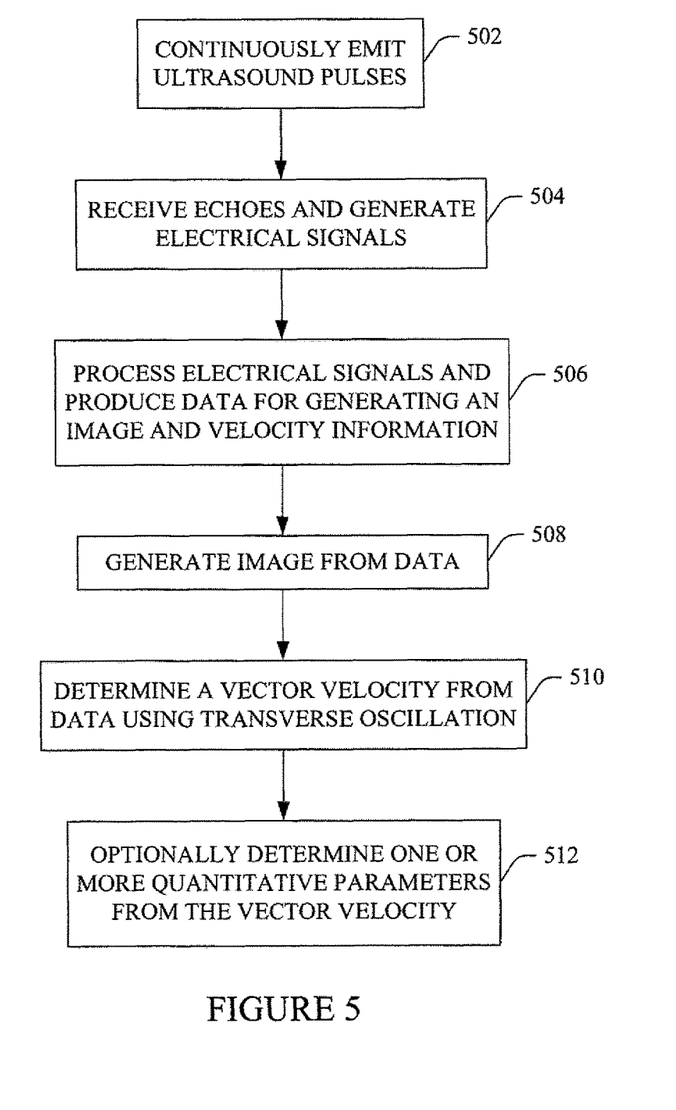
FIG. 5 illustrates a method in accordance with an embodiment disclosed herein.

FIG. 5 illustrates an example method for employing the ultrasound imaging system.

It is to be understood that the following acts are provided for explanatory purposes and are not limiting. As such, one or more of the acts may be omitted, one or more acts may be added, one or more acts may occur in a different order (including simultaneously with another act), etc.

At 502, ultrasound pulses are continuously emitted by the transducer array 102.

At 504, echoes, in response to the ultrasound signal, are received by the transducer array 102, and electrical signals indicative of the echoes are generated.

At 506, the electrical signals are processed to produce data for generating an image and for determining velocity via TO.

At 508, an image is generated with the data, as described herein and/or otherwise.

At 510, flow velocity is determined with the data, as described herein and/or otherwise. This includes setting a maximum measureable velocity, adjust the maximum measureable velocity range, concurrently measuring velocities, etc.

At 512, optionally, one or more quantitative measurements are determined based on the flow velocity, as described herein and/or otherwise.

The methods described herein may be implemented via one or more processors executing one or more computer readable instructions encoded or embodied on computer readable storage medium such as physical memory, which causes the one or more processors to carry out the various acts and/or other functions and/or acts. Additionally or alternatively, the one or more processors can execute instructions carried by transitory medium such as a signal or carrier wave.

The approached described herein is an improvement in the technology. The approach emits continuously in one direction, which yields continuous vector flow data, generated via TO VFI, which is used to determine one or more quantitative measurements such as velocity magnitudes, directions and/or profiles, and/or flow volume, flow turbulence and/or rotation, flow accelerations, pressure gradients, degrees of stenosis, and/or other quantitative measures. It also allows for measuring larger velocities than for spectral systems, which allows for a larger span of velocities to estimate than for traditional spectral techniques. It can replace the spectral display with much more accuracy and avoids errors from both the velocity angle and spectral broadening. The combination of function herein includes unconventional steps that confine the claim to a particular useful application.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    continuously transmitting, with a transducer array, an ultrasound signal in one direction;
    beamforming, with a beamformer, an echo signal received by the transducer array using a predetermined apodization function, wherein the echo signal is generated in response to an interaction of the ultrasound signal with flowing structure;
    estimating, with a velocity processor and using a transverse oscillation vector velocity estimation, a vector velocity of the flow, including velocity components, as a function of depth and time from the beamformed echo signal;
    estimating a maximum velocity based on $$v_{max} = \frac{\lambda_x f_{prf}}{4},$$

where $v_{max}$ is the maximum velocity, $\lambda_x$, is a lateral wavelength, and $f_{prf}$ is a pulse repetition frequency;
    generating, with a measurement processor, a quantitative measurement from the velocity components; and
    visually displaying, with a display monitor, the quantitative measurement.

2. The method of claim 1, further comprising:
    generating a B-mode image from the beamformed echo signals; and
    displaying the B-mode image with graphical indicia representing the quantitative measurement overlaid over the B-mode image.

3. The method of claim 1, where the transducer array is a 1-D array and the velocity components include an axial velocity component and a lateral velocity component.

4. The method of claim 1, where the transducer array is a 2-D array and the velocity components include an axial velocity component, a lateral velocity component and an elevation velocity component.

5. The method of claim 1, further comprising:
    adjusting a range of the maximum velocity by changing a distance between peaks in the apodization function.

6. The method of claim 1, wherein the apodization function includes a first apodization function and a second different apodization function, and further comprising:
    concurrently estimating a first velocity using the first apodization function and estimating a second velocity using the second different apodization function.

7. The method of claim 1, further comprising:
    adjusting a parameter of the apodization function over time to generate both a high systolic velocity and a low diastolic velocity from the echo signal.

8. The method of claim 1, further comprising:
    determining a velocity profile from the velocity components along a measurement direction.

9. The method of claim 8, further comprising:
    determining a volume flow from the velocity profile.

10. The method of claim 8, further comprising:
    determining a presence or absence of laminar flow from the velocity profile.

11. The method of claim 1, further comprising:
    determining a first velocity of the vector velocity before a stenosis in a vessel;
    determining a second velocity of the vector velocity at the stenosis in the vessel;
    and determining a degree of stenosis in the vessel from a ratio of the first velocity to the second velocity.

12. The method of claim 1, further comprising:
    determining a temporal acceleration of flow and a spatial acceleration of flow from the vector velocity; and
    determining a pressure gradient in a vessel by solving the Navier-Stokes equation using the temporal acceleration of flow and the spatial acceleration of flow.

13. An ultrasound imaging system, comprising:
    a transducer array configured to continuously transmit an ultrasound signal in one direction;
    a beamformer configured to beamform echo signals received by the transducer array using a predetermined apodization function;
    a velocity processor configured to determine a vector velocity of flow, including velocity components, from the beamformed echo signals using transverse oscillation vector velocity estimation, and estimate a maximum velocity based on $$v_{max} = \frac{\lambda_x f_{prf}}{4},$$

where $v_{max}$ is the maximum velocity, $\lambda_x$, is a lateral wavelength, and $f_{prf}$ is a pulse repetition frequency;
    a measurement processor configured to generate a quantitative measurement from the velocity components; and a display that visually presents the quantitative measurement.

14. The system of claim 13, where the velocity components are from a group consisting of an axial velocity component, a lateral velocity component and an elevation velocity component.

15. The system of claim 13, further comprising:
a controller that determines a range of the maximum velocity by changing the lateral wavelength by changing a distance between peaks in the apodization function, wherein the maximum velocity is on an order of four to eight times a maximum velocity determined from an axial wavelength.

16. The system of claim 13, wherein the measurement processor determines a velocity profile from the vector velocity.

17. The system of claim 16, wherein the display displays the velocity profile as arrows superimposed on a B-mode image.

18. The system of claim 16, wherein the measurement processor determines a volume flow for a vessel directly from the velocity profile.

19. The system of claim 16, wherein the measurement processor determines a velocity magnitude as a function of time or depth from the vector velocity from the velocity profile.

20. The system of claim 16, wherein the measurement processor determines a velocity angle as a function of time or depth from the vector velocity from the velocity profile.

21. The system of claim 20, wherein the measurement processor detects a presence of laminar flow from the velocity angle as a function of time, wherein a lack of deviations from a mean of the angle over time indicates laminar flow.

22. The system of claim 20, wherein the measurement processor detects an absence of laminar flow from the velocity angle as a function of time, wherein deviations from a mean of the angle indicates turbulent flow.

23. The system of claim 13, wherein the measurement processor determines a degree of stenosis in a vessel from a ratio between vector velocities measured before and at a stenosis.

24. The system of claim 13, wherein the measurement processor determines a pressure gradient in a vessel by solving the Navier-Stokes equation.

25. An apparatus, comprising:
a beamformer configured to beamform, using on a predetermined apodization function, echo signals received by a transducer array of an ultrasound imaging system, wherein the echo signals are generated in response to an interaction of anatomical tissue and an ultrasound signal continuously transmitted by the transducer array in one direction, wherein the apodization function includes a selectable parameter that controls a maximum measurable velocity;
a controller that sets the selectable parameter;
a processor configured to determine, using transverse oscillation vector velocity estimation, a vector velocity, including velocity components, from the beamformed echo signals, and estimate a maximum velocity based on $$v_{max} = \frac{\lambda_x f_{prf}}{4},$$

where $v_{max}$ is the maximum velocity, $\lambda_x$ is a lateral wavelength, and $f_{prf}$ is a pulse repetition frequency;
a measurement processor configured to generate a quantitative measurement from the velocity components;
and a display that visually presents the quantitative measurement.

26. The apparatus of claim 25, wherein the controller adapts the parameter over time to generate both a high velocity vector with a first value and a low velocity vector with a second value from the same data, wherein the first values is greater than the second value.

27. The apparatus of claim 25, wherein the apodization function includes a first apodization function and a second different apodization function, and the controller sets a first parameter value for the first apodization function and a second parameter value for the second apodization function to concurrently determine first and second different vector velocities.

* * * * *